(12) United States Patent
Perng (10) Patent No.: US 10,449,536 B2
(45) Date of Patent: Oct. 22, 2019

(54) DIAGNOSTIC DEVICES WITH MODIFIABLE HYDROPHOBIC SURFACES

(71) Applicant: Siemens Healthcare Diagnostics Inc., Tarrytown, NY (US)

(72) Inventor: John Perng, Newton, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 182 days.

(21) Appl. No.: 15/506,435

(22) PCT Filed: Aug. 31, 2015

(86) PCT No.: PCT/US2015/047715
§ 371 (c)(1),
(2) Date: Feb. 24, 2017

(87) PCT Pub. No.: WO2016/036658
PCT Pub. Date: Mar. 10, 2016

(65) Prior Publication Data
US 2017/0246627 A1   Aug. 31, 2017

Related U.S. Application Data

(60) Provisional application No. 62/045,707, filed on Sep. 4, 2014.

(51) Int. Cl.
*B01L 3/00* (2006.01)
*C12Q 1/25* (2006.01)
(Continued)

(52) U.S. Cl.
CPC ......... *B01L 3/5027* (2013.01); *B01L 3/50273* (2013.01); *B01L 3/502707* (2013.01);
(Continued)

(58) Field of Classification Search
CPC .. B01L 3/5017; B01L 3/5027; B01L 3/50273; B01L 2200/0621;
(Continued)

(56) References Cited

U.S. PATENT DOCUMENTS 6,019,944 A   2/2000   Buechler
6,902,705 B1  6/2005   Caillat et al.
(Continued)

FOREIGN PATENT DOCUMENTS

JP   2005140681 A   6/2005
WO       9315218 A1   8/1993
(Continued)

OTHER PUBLICATIONS

International Search Report and Written Opinion of International Application No. PCT/US2015/047715 dated Jan. 19, 2016.
European Search Report and Written Opinion of European Application No. 15838595 dated Jul. 26, 2017.

*Primary Examiner* — William H. Beisner
(74) *Attorney, Agent, or Firm* — Dunlap Codding P.C.

(57) ABSTRACT

A diagnostic device 10 for screening for a target analyte in a sample is provided. The diagnostic device 10 comprises a substrate 12 and a hydrophobic material 20 disposed on the substrate. The hydrophobic material 20 is selected to be converted from the hydrophobic material 20 to a hydrophilic material 22 upon contact with a conversion component within or derived from a sample introduced to the device 10.

18 Claims, 3 Drawing Sheets

(51) Int. Cl.
  *C12Q 1/26* (2006.01)
  *C12Q 1/34* (2006.01)
  *C12Q 1/54* (2006.01)
  *C12Q 1/58* (2006.01)
  *C12Q 1/40* (2006.01)
  *G01N 27/447* (2006.01)

(52) U.S. Cl.
  CPC ............... *C12Q 1/25* (2013.01); *C12Q 1/26* (2013.01); *C12Q 1/34* (2013.01); *C12Q 1/40* (2013.01); *C12Q 1/54* (2013.01); *C12Q 1/58* (2013.01); *C12Y 101/03004* (2013.01); *C12Y 113/12004* (2013.01); *C12Y 302/01108* (2013.01); *C12Y 305/01005* (2013.01); *C12Y 305/0201* (2013.01); *C12Y 305/03003* (2013.01); *B01L 2200/0621* (2013.01); *B01L 2300/0816* (2013.01); *B01L 2300/0851* (2013.01); *B01L 2300/0864* (2013.01); *B01L 2300/0887* (2013.01); *B01L 2300/165* (2013.01); *B01L 2400/0406* (2013.01); *G01N 27/447* (2013.01)

(58) Field of Classification Search
  CPC ....... B01L 2300/0864; B01L 2300/161; B01L 2300/165; B01L 2400/0688
  See application file for complete search history.

(56) References Cited

U.S. PATENT DOCUMENTS

| | | |
|---|---|---|
| 2008/0234659 A1 | 9/2008 | Cheng et al. |
| 2008/0248263 A1 | 10/2008 | Kobrin |
| 2008/0268287 A1 | 10/2008 | Donadio et al. |
| 2013/0224848 A1 | 8/2013 | Gandini et al. |
| 2015/0005193 A1* | 1/2015 | Phillips ............... C12Q 1/26 506/11 |

FOREIGN PATENT DOCUMENTS

| | | |
|---|---|---|
| WO | 2012024658 A2 | 2/2012 |
| WO | 2015164112 A1 | 10/2015 |

* cited by examiner

DIAGNOSTIC DEVICES WITH MODIFIABLE HYDROPHOBIC SURFACES

The subject application claims benefit under 35 USC § 119(e) of U.S. Provisional Application No. 62/045,707 filed Sep. 4, 2014. The entire contents of the above-referenced patent application are hereby expressly incorporated herein by reference.

FIELD

The present invention relates to the field of disposable, multi-purpose diagnostic testing devices and to methods of manufacturing the same.

BACKGROUND

Low cost, robust, and sensitive diagnostic tests are needed for resource limited settings. However, most point of care diagnostic tests currently on the market require a reader, a power source, and an electronic display to output the results, all of which significantly add to the cost of performing the test. Although some colorimetric test strips can be operated without the use of auxiliary electronics, user interpretation is still required and the results may vary from patient to patient. Accordingly, diagnostic devices that are inexpensive, equipment-free, portable, sensitive, with easy-to-read results would be desirable.

SUMMARY

Aspects of the present invention are directed to easy-to-produce and customizable diagnostic devices. The devices may be utilized for health-related diagnostic tests for the detection of glucose, lactose, urea, creatinine, and the like in a biological sample, for example. Advantageously, the devices may be quickly manufactured and do not require equipment to provide at least qualitative or semi-quantitative results. Thus, the devices described herein may be utilized where resources are limited. Further, the devices described herein may be inexpensively constructed from low cost materials, are simple to manufacture, are highly flexible (in terms of assay expansion), require only small sample sizes, and provide fast results.

In accordance with one aspect, there is provided a diagnostic device which utilizes a conversion component to provide at least a qualitative or semi-qualitative result for a target analyte or property in the sample. In certain aspects, the conversion component comprises a target analyte in a sample which directly reacts with a hydrophobic material associated with the device to convert the hydrophobic material to a hydrophilic material.

In accordance with another aspect of the present invention, the conversion component may comprise a compound which is derived from a target analyte in the sample. For example, the conversion component may comprise or be derived from a product of a reaction with a target analyte in a sample, wherein the produced conversion component from the reaction with the target analyte is effective to convert a hydrophobic material associated with the device to a hydrophilic material. In exemplary embodiments, the conversion component may comprise $H_2O_2$, $CO_2$, or another component produced via an enzymatic reaction with a target analyte in a sample such as glucose, lactose, urea, and creatinine. Via a number of different structures and arrangements described herein, the presence of the target analyte may be quickly and inexpensively determined qualitatively, semi-quantitatively, or even quantitatively.

In accordance with another aspect, there is provided a device including one or more reaction channels, each of which may include a hydrophobic material associated therewith. The hydrophobic material is selected such that upon contact with a conversion component (e.g., a target analyte or a product from a reaction with a target analyte in a sample), the hydrophobic material is converted from the hydrophobic material to a hydrophilic material. The device may be structured so as to provide an indication of the extent of the hydrophobic to hydrophilic conversion caused by the conversion component, which may correspond to the amount of a target analyte in the sample.

In accordance with another aspect, the hydrophobic material may be converted to the hydrophilic material by the conversion component so as to allow a hydrophilic or aqueous sample to move up the reaction channel as the conversion takes place. In certain embodiments, one or more enzymes may also be provided along with the hydrophobic material within one or more reaction channels to produce a conversion component, e.g., $H_2O_2$ or $CO_2$, which may convert the hydrophobic material to a hydrophilic material.

In accordance with another aspect, as the concentration of the target analyte increases in a sample, a greater amount of hydrophobic to hydrophilic conversion takes place. The extent of conversion may be utilized to quickly determine at least qualitatively or semi-quantitatively (e.g., provide a range for a target analyte or whether a predetermined threshold value has been reached or not) an amount of a target analyte in a sample. For example, reaction channels having differing concentrations of the hydrophobic material may be provided in a device. In other embodiments, a plurality of channels may be provided, each with a different length to determine an amount of an analyte in a sample. In still other embodiments, the device may comprise a plurality of channels, each with a different concentration of one or more compounds, such as one or more enzymes, which will react with a target analyte in a sample to at least quantitatively or semi-quantitatively provide an indication of an amount of the target analyte in the sample.

In accordance with another aspect, the device may further include a dye that directly or indirectly provides an indication of an amount of the target analyte in the sample. The dye may be placed along a path of the reaction channel or at an end thereof. For example, the dye can be placed at an end of a reaction channel and provide an indication that hydrophobic to hydrophilic conversion has taken place to a degree sufficient for the sample to reach the dye. In other embodiments, the dye may be distributed entirely or at intervals along a length of each reaction channel. The dye may be selected such that upon contact with a conversion component such as hydrogen peroxide, nitric oxide, or a thiol-terminated group, the dye undergoes a reaction and provides visible or readable color change. In other embodiments, the dye is selected such that it provides an indication that an aqueous sample has come into contact therewith.

Below are described exemplary embodiments of the devices that may be produced in accordance with aspects of the present invention, but it is understood that the present invention is not so limited.

BRIEF DESCRIPTION OF THE DRAWINGS

The invention is explained in the following description in view of the drawings that show.

DETAILED DESCRIPTION

In accordance with one aspect of the present invention, there is provided a diagnostic device comprising a substrate and a hydrophobic material disposed on the substrate. The hydrophobic material is a material that will be converted from the hydrophobic material to a hydrophilic material upon contact with a conversion component within or derived from a sample introduced to the device. In an embodiment, the conversion component comprises a compound such as hydrogen peroxide produced from one or more enzymatic reactions starting with a target analyte in a sample introduced into the device.

In accordance with another aspect of the present invention, there is provided a diagnostic device comprising a substrate; a plurality of reaction channels defined on the substrate; a hydrophobic material disposed within at least one the reaction channels; and one or more enzymes disposed within at least one of the reaction channels along with the hydrophobic material. The one or more enzymes are selected to provide a conversion component upon contact of the one or more enzymes with a target analyte in a sample introduced to the device. The hydrophobic material is selected to be converted from the hydrophobic material to a hydrophilic material on the substrate upon contact with the conversion component.

In accordance with another aspect of the present invention, there is provided a diagnostic device comprising a substrate; a plurality of reaction channels defined on the substrate; one or more enzymes disposed within selected ones of the reaction channels; and a dye associated with selected ones of the reaction channels. The dye may be disposed at ends of the selected reaction channels, at intervals along selected reaction channels, or throughout selected ones of the reaction channels, for example. "Selected ones" may refer to any one or more of the reaction channels. The one or more enzymes are selected to provide a conversion component upon contact of the one or more enzymes with a target analyte in a sample introduced to the device. In an embodiment, the dye provides a visible or readable change in a property thereof upon reaction with the conversion component, which may be a color or fluorescence change, for example. In other embodiments, the dye may produce a visible or readable change upon mere contact with the conversion component. To provide at least a qualitative or semi-quantitative result, the device may comprise a plurality of reaction channels, each with a different amount of the one or more enzymes therein. In another embodiment, the device may comprise a plurality of reaction channels with equivalent concentrations of the one or more enzymes, but with different concentrations of the dye material.

As used herein, the term "conversion component" may refer to any compound which is effective to convert an amount of a hydrophobic material to an amount of the hydrophilic material and/or produce a change in a dye material as described herein.

As used herein, by the phrase "effective amount," it is meant an amount of material suitable for bringing about an intended result.

As used herein, the term "sample" refers to any material that contains a target for which a target assay is desired. The sample can be but is not limited to a biological sample, such as a biological fluid or a biological tissue.

As used herein, the term "subject" refers to any human and non-human mammal.

Figure 1A:
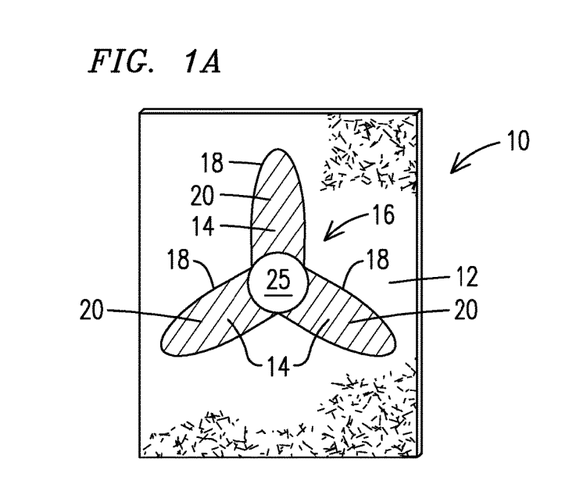
FIGS. 1A-1B illustrate a diagnostic device having a surface that is modifiable from a hydrophobic surface (FIG. 1A) to a hydrophilic surface (FIG. 1B).
Figure 1B:
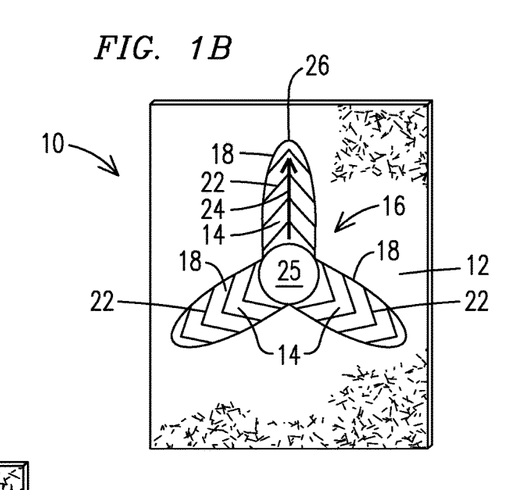

Referring now to the figures, FIGS. 1A-1B illustrate a diagnostic device 10 in accordance with an aspect of the present invention. The device 10 comprises a base member 12 and at least one reaction channel 14 defined on the base member 12 in a predetermined pattern 16. For purposes of illustration, a plurality of reaction channels 14 may be provided on a single device as shown in FIG. 1, although it is understood that the present invention is not so limited. It is contemplated that a device may comprise a single reaction channel 14 and may be in the form of a strip. When a plurality of reaction channels 14 are provided, the reaction channels 14 may be separated from one another by providing a boundary for each reaction channel. In certain embodiments, for example, at least a portion of the periphery of each reaction channel 14 is defined by a barrier defining material 18 (hereinafter "barrier material 18"). An effective amount of a hydrophobic material 20 may be disposed within at least a portion of each reaction channel 14 defined by the barrier material 18.

Critically, the hydrophobic material 20 is selected to have a structure such that upon contact with a conversion component, the hydrophobic material 20 is converted from the hydrophobic material 20 as shown in FIG. 1A to a hydrophilic material 22 as shown in FIG. 1B. It is understood that by "conversion from hydrophobic material to hydrophilic material" or the like it is meant that upon reaction with the conversion component, the hydrophobic material becomes more hydrophilic than prior to contact with the conversion component.

In an embodiment, the conversion component may comprise a target analyte in the sample introduced into the device 10. In another embodiment, the conversion component may comprise a product derived from the target analyte. For example, the conversion component may be produced from a reaction with a target analyte in the sample introduced into the device 10. In still another embodiment, the conversion component may comprise a product of a reaction with a compound derived from the target analyte such as with an intermediate product from a reaction starting with the target analyte. It is understood that it may not be known whether the target analyte is present in an unknown sample. As the hydrophobic material 20 is converted to the hydrophilic material 22 by the conversion component along a length of a respective reaction channel 14, an aqueous sample may travel along a longitudinal length of the reaction channel 14 by capillary action in the direction shown by arrow 24.

In certain embodiments, if the sample does not include or provide a sufficient amount of the target analyte to directly or indirectly convert the hydrophobic material 20 in the reaction channel 14 to the hydrophilic material 22, the sample will not travel from a sample port 25, for example, to an end 26 of the reaction channel 14 as shown in FIG. 1B, for example. To the contrary, if the sample comprises a sufficient amount of the target analyte, the hydrophobic material 20 will be converted to the hydrophilic material 22 along an entire length of the respective reaction channel 14 and reach the end 26.

It is appreciated that the sample to be introduced into the device 10 may comprise any one or more of urine, saliva, and blood, or a sample derived therefrom, from a subject. Further, the sample to be introduced into the device 10 may undergo any pre-treatment or filtration process as is known in the art in preparation for analysis prior to introduction to the device 10.

The base member 12 may be any suitable porous or non-porous material. In certain embodiments, the base member 12 comprises a porous material. The porous material may comprise a cellulosic material, a glass fiber material, a porous polymeric material, or combinations thereof, for example. With a porous material, it is generally understood that the barrier material 18, hydrophobic material 20, and any other desired components for the device 10 may be disposed on a surface of the base member 12 and/or within pores of the base member 12.

While not shown in the Figs., a cover layer may be used to cover the device 10 (and any of the other devices discussed below) thereby enclosing one or more, up to all, of reaction channels 14 from above. State differently, the cover layer may position opposite the base member 12 with the reaction channel disposed in between. Thus individual reaction channels 14 can be defined by base member 12, the barrier material 18, and the cover layer. Any such cover layer would have an opening aligned with the sample port 25 to allow for sample entry. The cover layer could be made from any of a variety of transparent materials known to a person of ordinary skill in the art such that the reaction channel 14 remains visible below. Such a cover layer may help protect a user from coming into contact with the sample.

In the embodiment shown in FIGS. 1A-1B, there are shown three reaction channels 14 which define the pattern 16. However, it is understood that the present invention is not so limited and any number of reaction channels 14 may be defined on the base member 12. For example, the device 10 may be patterned so as to provide a device with one, four, six, eight, ten or any other number of reaction channels 14. In addition, the channels 14 may be of any suitable length and width to accomplish the objectives of the assay to be performed within each reaction channel 14. In an embodiment, selected ones of the reaction channels 14 comprise a predetermined amount of the hydrophobic material 20 therein, although it is contemplated the devices described herein are not so limited. In certain embodiments, it may be desirable to provide a control reaction channel 14 having no hydrophobic material 20 therein, for example.

Advantageously, the simple construction of the devices described herein enable easy assay expansion. For example, if one wished to expand the device 10 to accommodate three additional concentrations of the hydrophobic material 20 in the reaction channels 14, one could do so by defining adding additional reaction channels 14 to the pattern 16 in FIG. 1A and disposing a predetermined amount of hydrophobic material 20 (and any other suitable components) within the additional channels. It is appreciated that device 10 may be tailored so as to accommodate two or more distinct hydrophobic materials and/or other components, each of which may be directly or indirectly useful in testing for one or more target analytes in a sample introduced to the device 10.

When multiple reaction channels 14 are present, the reaction channels 14 may be defined on the base member 12 by any suitable method, such as by drawing, spraying, brushing, and/or printing the barrier material 18 in the desired pattern 16 on the base member 12. In an embodiment, the reaction channels 14 may be defined by disposing the barrier material 18 on a single side of the device 10 in the pattern 16. In other embodiments, the reaction channels 14 may be defined by disposing the barrier material 18 on both sides of the base member 12. In certain embodiments, the reaction channels 14 may be disposed on opposed sides in substantially the same pattern 16, although the present invention is not so limited. It is appreciated that a non-porous material may be placed between the two opposed sides at least where penetration of the sample from one side to other is not desired. In an embodiment, a sample introduction site is located or provided on the base member 12 for the introduction of the sample to the device 10 to provide sufficient sample for one or both sides of the device 10. For example, the device 10 may comprise a single, common sample introduction site 25 for the device 10 such that a sample introduced to the site 25 is sufficient to provide sample for each of the reaction channels 14 on the device 10 as shown in the FIGS.

The barrier material 18 may be any suitable material effective to form a barrier to a sample introduced into the device 10 and define a path (e.g., a reaction channel 14) for the sample when the hydrophilic material 20 is converted to the hydrophobic material 22. In an embodiment, the barrier material 18 has a lower porosity and/or a higher degree of hydrophobicity than the base member 12 and/or the hydrophilic material 22 (when present and converted from the hydrophobic material 20). In this way, a sample may continue to be maintained within a boundary defined by the barrier material 18. Thus also, the barrier material 18 is typically a hydrophobic material that is not converted to the hydrophilic material 22 by contact with the sample or components in the reaction channel 14. In certain embodiments, the barrier material 18 may comprise one or more components selected from the group consisting of hydrophobic polymers, permanent inks, waxes, or any other suitable hydrophobic material.

The hydrophobic material 20 may be any suitable material that is converted to a hydrophilic material 22 by contact with a conversion component as described herein. In an embodiment, the hydrophobic material 20 may be provided in an amount effective to indicate the presence of a target analyte in a sample. In an embodiment, upon conversion of the hydrophobic material 20 to hydrophilic material 22 within a respective reaction channel 14, a sample introduced at a leading edge of the reaction channel 14 will be able to flow by capillary action along a longitudinal length of the reaction channel 14 to a degree commensurate with the extent of hydrophobic material conversion. In other words, if there is a sufficient amount of the target analyte, the hydrophobic to hydrophilic conversion may take place over the entire length of the respective channel 14. As noted above, in certain embodiments, the conversion component may comprise the target analyte in the sample which is introduced onto the device. In other embodiments, the conversion component is formed from a reaction with a target analyte or a reaction with a product of another reaction stemming from the target analyte.

By way of example, the hydrophobic to hydrophilic conversion may be stimulated via reactions with $H_2O_2$, $CO_2$, compounds with thiol-terminated groups such as glutathione (GSH), or a change in pH, for example. The following are non-limiting exemplary starting materials and reaction schemes for the hydrophobic to hydrophilic material conversion in accordance with an aspect of the present invention. It is understood, however, that the present invention is not so limited to these examples.

In an embodiment, the hydrophobic material 20 is selected so as to be one that may be converted to a hydrophilic material 22 through contact with hydrogen peroxide as shown below, for example. As such, the conversion of the hydrophobic material 20 to the hydrophilic material 22 may be done via an oxidation-triggered reaction. In the exemplary reaction below, the hydrophobic material 20 is shown on the left side of the reaction scheme and the hydrophilic material 22 is shown on the right of the reaction arrow.

(I) $H_2O_2$ Stimulated Reactions

In another embodiment, an alkyl ketene dimer may be added to the reaction channels 14 to modify a hydrophilic surface of the base member 12 to a hydrophobic surface. Introduction of a sample that includes or directly or indirectly produces an amount of a conversion component such as $H_2O_2$ via reaction could thereafter reverse the wettability of the modified surface to a hydrophilic surface. The now hydrophilic surface allows the sample to travel up the reaction channel 14 to a degree commensurate with the amount of the target analyze that produces the conversion component (e.g., $H_2O_2$).

Hydrophilic

(II) $CO_2$ Stimulated Reaction

In another embodiment, the hydrophobic material 20 may comprise a composition which is converted to the hydrophilic material 22 via reaction with at least $CO_2$. For example, the hydrophobic material 20 may comprise a compound comprising amidine functional groups. In a particular embodiment, for example, the hydrophobic material 20 comprises an amidine-terminated self-assembled monolayer coated on a surface that may be converted to a hydrophilic material 22 in the presence of $CO_2$ and water as shown below.

Hydrophobic

$\downarrow H_2O_2$

(III) pH Stimulated Reaction

In another embodiment, the hydrophobic material 20 may comprise a compound having one or more pH-sensitive functional groups such that the device 10 may be utilized to determine a pH of a sample, such as a blood or urine sample. For example, the hydrophobic material 20 may comprise a compound having a carboxyl group, pyridine, imidazole, dibuthylamine, or tertiary amine methacrylate. Further examples include (a) Poly(acrylic acid) (PAAc); (b) poly (methacrylic acid) (PMAAc); (c) poly(N,N'-diethyl aminoethyl methacrylate) (PDEAEMA); (d) Poly(4-vinylpyridine) (P4VP); (e) Poly(vinyl imidazole) (PVI); and (f) poly[2-(methacryloyloxy)-ethyltrimethylammonium chloride] (PMETAC).

In still another embodiment, the hydrophobic material 20 may comprise a compound having a functional group selected from (a)-(f) below. In the embodiments shown below, n may=from 1 to 1000 or more. Via oxidation of the carboxyl group, for example, the hydrophobic material 20 may be converted into the hydrophilic material 22 and thereby indicate a pH or pH range of a sample.

In still another embodiment, the hydrophobic material 20 may comprise an acid-base catalyzed acetal compound ((g) below), which may undergo the following reaction to provide an indication of a pH or a pH range of a sample. As can be seen, the lower the pH of a sample, the greater the amount of hydrogen ions available for conversion to a more hydrophilic compound. In the following example, $R^1$ and $R^2$ may be any suitable hydrophobic group. In a particular embodiment, $R^1$ and $R^2$ may be independently an unsubstituted or substituted straight-chained or branched alkyl group or an aryl group, for example.

(IV) Thiol Stimulated Reaction

Figure 2:
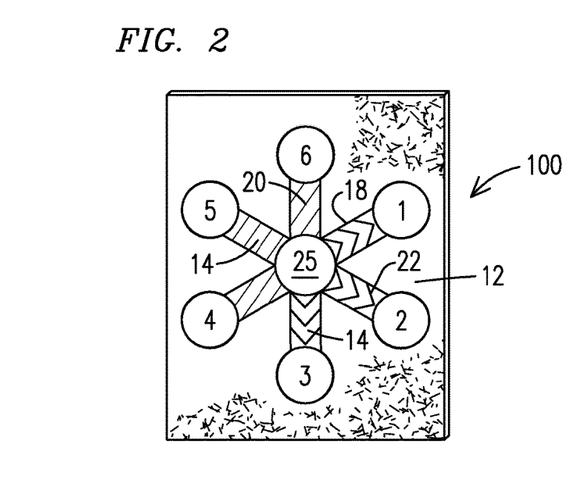
FIG. 2 illustrates a diagnostic device having multiple reaction channels in accordance with an aspect of the present invention.

In another embodiment, the hydrophobic material 20 may comprise a compound which converted to the hydrophobic material 22 by reaction with a thiol compound. In certain embodiments, the hydrophobic material 20 may be converted to the hydrophilic material 22 via cleavage of a disulfide bond. For example, the conversion component may comprise glutathione (GSH), which may be found in a blood sample, which will cleave the disulfide bond of the hydrophobic material 20. Thus, in an embodiment, the hydrophobic material 20 may be a compound, which when contacted by GSH, is converted into the hydrophilic material 22. In some embodiments, the glutathione is targeted directly to determine a qualitative, semi-quantitative or quantitative amount of GSH in a sample. In other embodiments, the hydrophobic material 20 may be selected so as to react with a thiol compound in the sample merely to allow the sample to move up the length of the reaction channel where another qualitative, semi-quantitative, or quantitative assay may take place. In a particular embodiment, the hydrophobic compound 20 may be converted to a hydrophilic material 22 by reaction with a thiol such as RSH as follows:

In accordance with an aspect of the present invention, when multiple reaction channels 14 are provided, the plurality of channels 14 may comprise channels 14 having different concentrations of the hydrophobic material 20 therein. For example, a device 100 having a six channel configuration is shown in FIG. 2 (numbered 1-6 in a clockwise direction). Selected ones of the reaction channels 14 may be provided with different concentrations of the hydrophobic material 20. A control reaction channel 14 with no hydrophobic material may also be provided. In certain embodiments, the channels 14 may have an increasing concentration of the hydrophobic material 20, for example, from channels 2-6 with one channel (e.g., channel 1) serving as a control. In operation, there may be a sufficient amount of the hydrophobic material 20 in the sample to cause an entire length of one reaction channel 14 (e.g., a channel having 0.5 mM of the hydrophobic material) to be converted from the hydrophobic material 20 to the hydrophilic material 22 by the conversion component, but not the next greater "level" or concentration of hydrophobic material (e.g., 1.0 mM). With these results, it would be understood that there is an amount of the conversion component sufficient to convert from 0.5 mM to <1.0 mM of hydrophobic material 20. The amount of the target analyte may be determined therefrom as would be readily understood by one skilled in the art.

Figure 3:
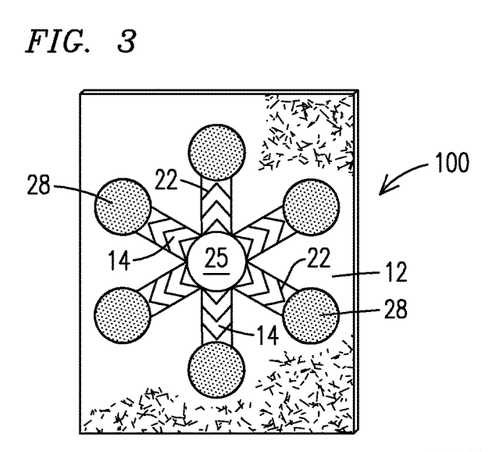
FIG. 3 illustrates a diagnostic device having a dye at an end of each reaction channel in accordance with an aspect of the present invention

In certain embodiments, the conversion of hydrophobic material 20 to hydrophilic material 22 may itself provide a colorimetric result which can be visually inspected or read by suitable apparatus to determine an amount of hydrophobic to hydrophilic conversion. The extent of hydrophobic to hydrophilic conversion may then be correlated with the amount of a target analyte in a sample. In other embodiments, the conversion of hydrophobic to hydrophilic conversion does not itself provide a measurable indication. Therefore, in any of the embodiments described herein, an effective amount of a dye 28 may be disposed at an end of the one or more reaction channels 14 to indicate when an entire length of the reaction channel 14 has been converted from the hydrophobic material 20 to the hydrophilic material 22 as is exemplified by FIG. 3. In this way, the sample will have traveled up an entire longitudinal length of the respective reaction channel 14. Upon contact of the aqueous sample material with the dye 28, the dye 28 will provide an indication of the presence of a sufficient amount of the predetermined compound to convert the hydrophobic material 20 to the hydrophilic material 22 within the corresponding reaction channel 14.

The dye 28 may be any suitable material capable of providing a readable or visible indication upon contact with the sample. In an embodiment, the dye 28 does not react with any component associated with the sample, but is capable of providing a visible or readable indication that the sample has come in contact therewith. In other embodiments, the dye 28 may be selected so as to also react with a conversion component (e.g., hydrogen peroxide, nitric oxide, or a compound having a thiol-terminated group) to provide a qualitative, semi-quantitative, or quantitative indication that the conversion component has come into contact therewith. Thus, in another aspect, the conversion component may be a component which reacts with the dye to produce a measurable change in the dye 28. The change may be visible based on a hue, or may be a readable change such as a change in fluorescence of the dye upon contact with the conversion component. Exemplary dyes 28 that can be triggered by reaction with hydrogen peroxide, for example, and result in fluorescence increase are shown (h)-(k). Exemplary dyes 28 that can be triggered by reaction with thiol-terminated groups and result in fluorescence increase are shown (l)-(o).

Hydrogen Peroxide-Triggered Fluorescence

Thiol-Triggered Fluorescence

The following compounds contain the same carbamate group that can be removed by thiol, such as glutathione (GSH). They share the same reaction mechanism.

Nitric Oxide (NO)-Triggered Fluorescence

The following compounds involve NO-induced diamine cyclization process, and fluorophores attached to phenyl-diamine become fluorescent when reacting with NO. They share the same reaction mechanism.

Figure 4:
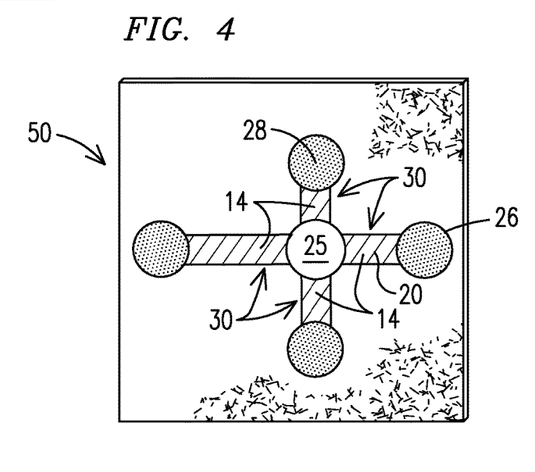
FIG. 4 illustrates a diagnostic device having arms of different lengths in accordance with an aspect of the present invention.

Now referring to FIG. 4, there is shown a device 50 comprising a plurality of channels 14 having the same concentration of hydrophobic material 20 therein, but have differing lengths 30. By way to comparison of known standards of a predetermined compound, a qualitative or semi-qualitative analysis may be provided for the predetermined compound. For example, a known amount of analyte may be sufficient to cause the sample to travel an entire length of one reaction channel 14, but not another reaction channel 14. By comparison to known standards, a qualitative, semi-quantitative, or quantitative analysis may be provided for an unknown sample. As described above, a dye 28 may be disposed at an end 26 of the channel 14 if necessary to provide an indication that a sample has traveled from sample port 25 to the end 26.

In accordance with another aspect, any or more of the devices described herein may comprise reaction channels 14 comprising one or more enzymes which are specific for one or more target analytes (or products derived therefrom) in a sample to thereby directly or indirectly produce a conversion component which may react with a hydrophobic material 20 and/or dye to provide an indication of the presence of the target analyte in the sample.

In still another aspect, the devices described may not include a hydrophobic material 20 which is converted to a hydrophilic material, but instead include a substrate having one or more reaction channels with one or more enzymes disposed within a selected reaction channel or channels and a dye to provide an indication of the amount of conversion.

By way of example, the one or more enzymes may include enzymes for the breakdown of creatinine, glucose, lactose, urea, and the like in the sample. As such, the conversion component may be a product of an enzymatic reaction, such as hydrogen peroxide or carbon dioxide, which can react with the hydrophobic material 20. For example, in one embodiment, the enzymes may comprise enzymes, e.g., creatininase, creatinase, and sarcosine oxidase, for the breakdown of creatinine in the sample. The enzymes work according to the reaction:

(I)

In another embodiment, the enzymes may comprise one or more enzymes, e.g., glucose oxidase, for the breakdown of glucose in the sample according to the reaction:

(II)

In another embodiment, the enzymes may comprise one or more enzymes, e.g., lactate oxidase, for the breakdown of lactate in the sample according to the reaction:

(III)

In still another embodiment, the enzymes may comprise one or more enzymes, e.g., lactase and glucose oxidase, for the breakdown of lactose in the sample according to the reactions:

In still another embodiment, the enzymes may comprise one or more enzymes, e.g., urease, for the breakdown of urea in the sample according to the reaction:

(IV)

As mentioned, in certain embodiments, the enzymes produce a conversion component from a target analyte in the sample and the hydrophobic material 20 may be selected to be one that is converted from the hydrophobic material 20 to the hydrophilic material 22 as described herein via the conversion component. In certain embodiments, the conversion component such as the produced hydrogen peroxide may also or instead react with a dye 28 at an end 26 of a respective reaction channel 14 as was shown in FIG. 4. The dye 28 may provide a visible or readable indication that the enzymatic reaction (with the target analyte or a downstream product from a reaction with the target analyte) has taken place and that hydrogen peroxide has been produced throughout a length of the reaction channel 14.

Figure 5:
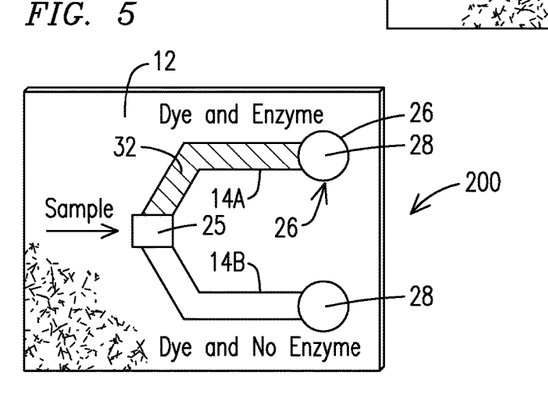
FIG. 5 illustrates a diagnostic device having an arm (reaction channel) with a dye and an enzyme and an arm (reaction channel) having a dye and no enzyme in accordance with an aspect of the present invention.

Referring now to FIG. 5, there is shown another embodiment of a device 200 having two reaction channels 14A and 14B. Reaction channel 14A comprises one or more enzymes 32 for the breakdown of a target analyte in a sample introduced into the device 200. In the embodiment shown, a sample may be introduced at sample inlet 25. If the sample includes the desired target analyte, the one or more enzymes 32 facilitate the breakdown of the target analyte to the conversion component through one or more steps in the reaction channel 14A, wherein the conversion component will react with a dye 28 which may be disposed within the channel (along the length) or at an end thereof as shown to provide a change in a property of the dye indicative of a presence of the target analyte.

For example, the conversion component may react with the dye 28 to provide a readable or visible indication if and when the sample has reached the dye 28 at the end of the reaction channel 14. Alternatively, the dye may be additionally or instead be distributed along a longitudinal length of each channel 14A, 14B from sample inlet 25 to end 28. In the embodiment shown in FIG. 5, reaction channel 14B does not comprise enzyme(s) and thus may serve as a control to correct for any unspecific reactions that may induce any color change in the sample. In certain embodiments, the dye 28 may comprise a hydrophobic material.

Figure 6:
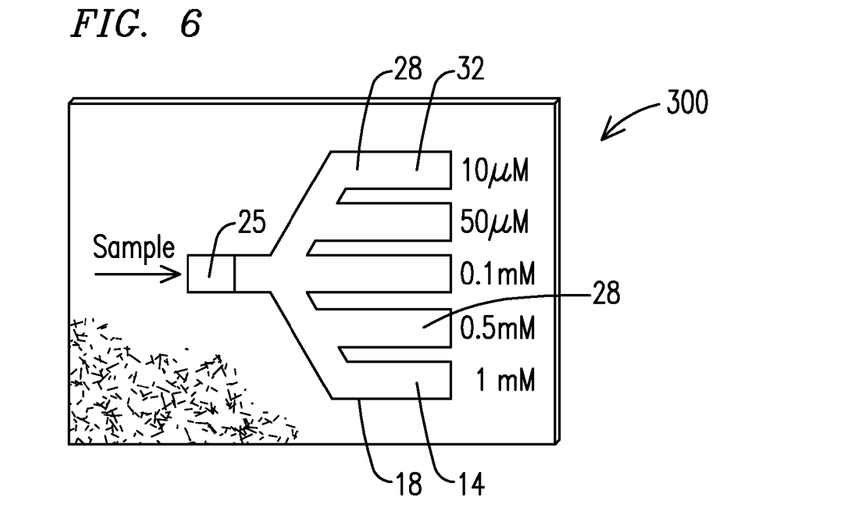
FIG. 6 illustrates a diagnostic device having reaction channels with different enzyme concentrations therein in accordance with an aspect of the present invention.
Figure 7:
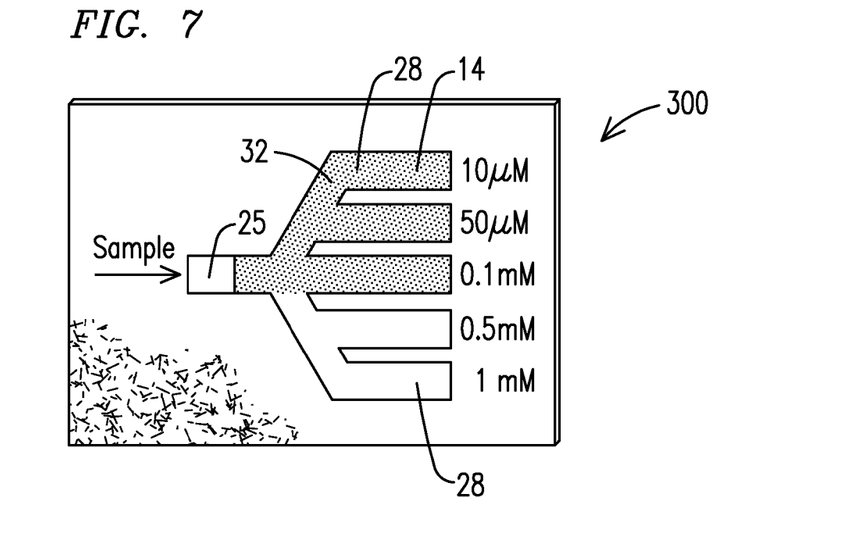
FIG. 7 illustrates the diagnostic device of FIG. 6 with a positive result in three of the five reaction channels, thereby providing a semi-quantitative information for a target analyte in a sample in accordance with an aspect of the present invention.

Referring now to FIG. 6-7, there is shown another embodiment of a device 300 in accordance with an aspect of the present invention having a plurality of reaction channels 14, each with differing concentrations of the one or more enzymes 32. For example, as shown, the device 300 in each of FIGS. 6-7 has five arms having 10 µM, 50 µM, 0.1 mM, 0.5 mM, and 1 mM of one or more enzymes 32. In the case of multiple enzymes, each reaction channel 14 may have the same concentration of enzymes or a differing amount. In addition, each channel 14 may include a dye 28 as described herein disposed uniformly within the reaction channel 14 bounded at least in part by the barrier material 18.

Once the sample is introduced onto sample introduction site 25, a readable or visible indication that the sample has contacted the dye 28 within a respective reaction channel 14 will only be produced if a target analyte in the sample, e.g., creatinine, fully reacts with the enzymes 32 in the reaction channel 14 to produce a conversion component that will react with the dye 28 to produce a color change, e.g., hydrogen peroxide. If the creatinine (in this case) is below the enzyme concentration, it is contemplated that no color change of the dye 28 will take place along the entire length of the reaction channel. Thus, with reference to FIGS. 6 and 7, it can be seen that the test results in FIG. 7 indicate that there was sufficient creatinine in the sample to produce an amount of hydrogen peroxide sufficient to provide a positive indication for the 10 µM, 50 µM, and 0.1 mM channels, but not 0.5 mM or 1 mM. Thus, it can be deduced that the unknown sample has creatinine content sufficient to react with between 0.1 mM to 0.5 mM of the enzyme(s) disposed in the channel 14.

In alternate embodiment, referring again to FIGS. 5-7, the reaction channels 14 may comprise the same concentration of the one or more enzymes 32, but selected ones of the reaction channels 14 may be provided with a different concentration of the dye 28 at an end thereof or along a longitudinal length of the channels 14. If the sample has a sufficient amount of a target analyte to produce a sufficient amount of the conversion component (via one or more enzymes) to react with the dye 28 in the channel, it may be determined from the dye 28 that the sample has at least a concentration of the target analyte which corresponds to the amount of dye 28 undergoing a color change in the respective channel. For example, all of the dye 28 at an end of the channel 14 or throughout a channel 14 may undergo a color change indicative of a presence of a corresponding amount of the target analyte.

In certain embodiments, the base member 12 shown in FIGS. 1A-1B, for example, is entirely self-supporting. In other embodiments, the devices described herein may be mounted on a backing. The backing may be formed from a liquid impermeable material, such as a polymeric material, for example. The base member 12 may be secured to the backing by any suitable structure such as tabs, clips, an adhesive, or the like. In still another embodiment, the base member 12 may be disposed (sandwiched) between a first backing and a second backing and secured thereto by any suitable structure or process, such as by laminating and/or the use of tabs, clips, an adhesive, or the like.

If a laminate structure is used to house the base member 12 between a first backing and a second backing, the laminate structure may comprise a commercially available laminate pouch made from a polymeric material and a suitable heat melt adhesive as is known in the art. In this embodiment, the base member 12 may positioned between the first backing and the second backing and the backings, base member, and reagent(s) may be collectively laminated under pressure and/or heat to form an enclosed device. In addition, in this embodiment, one or more first apertures may be provided in the backings to serve as a respective sample port for receiving a sample to be distributed to the reaction channels in fluid communication with the sample port. In addition, the device may comprise one or more second apertures disposed over any one or more of the reaction channels 14 to serve as respective vents in the device for allowing a sample to move up the reaction channels.

Once the sample has been introduced into a device as described herein and the desired duration has expired for the subject assay has been completed, the results may be determined by visual inspection or alternatively by other suitable methods and equipment known in the art. In certain embodiments, the assay result(s) may be readily determined as set forth above by having different concentrations in different reaction channels, for example. The results may then be compared to those of known standards as is known in the art that are determined concurrently or otherwise.

In certain embodiments, the assay results are colorimetric in nature and provide for example, a deeper or darker color with an increasing amount of the target analyte. In such cases, the assay results may be recorded by taking an image of the device after completion of the assay(s) thereon. The images can be recorded and stored on smart phones, scanners, cameras, and the like. In certain embodiments, an image is taken of the relevant portion of the device before and after the testing for comparison utilizing a suitable software program, such as the Eyedropper tool from Adobe Systems, Inc. Specific properties, such as intensity, can be measured from the recorded images and compared to values of a calibration curve created from known standards. In another embodiment, the samples may be read by fluorescence detection as is known in the art. In an embodiment, the recorded images may be transmitted and/or stored on a computer comprising a microprocessor comprising hardware or software configured for processing and analysis of the imaging data. In certain embodiments, the data and/or results may be transmitted remote site over a network.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The following in a non-limiting list of illustrative embodiments of the invention:

1. A diagnostic device comprising: a substrate; and a hydrophobic material disposed on the substrate; wherein the hydrophobic material is selected to be converted from the hydrophobic material to a hydrophilic material upon contact with a conversion component within or derived from a sample introduced to the device.

2. The diagnostic device of illustrative embodiment 1, wherein the conversion component is selected from the group consisting of hydrogen peroxide, carbon dioxide, and glutathione.

3. The diagnostic device of illustrative embodiment 1, wherein the conversion component comprises a target analyte in the sample.

4. The diagnostic device of illustrative embodiment 1, wherein the conversion component comprises a product derived from a reaction with a target analyte in the sample.

5. The diagnostic device of illustrative embodiment 1, wherein the conversion component comprises a component derived indirectly from the target analyte.

6. The diagnostic device of illustrative embodiment 1, wherein the target analyte is selected from the group consisting of glucose, lactose, urea, and creatinine.

7. The diagnostic device of illustrative embodiment 1, wherein the conversion component comprises a member selected from the group consisting of hydrogen peroxide and carbon dioxide.

8. The diagnostic device of illustrative embodiment 1, wherein the target analyte is selected from the group consisting of glucose, lactose, urea, and creatinine, and wherein the conversion component comprises a product from an enzymatic reaction with the target analyte or a derivative thereof.

9. The diagnostic device of any of the preceding illustrative embodiments, wherein the substrate comprises a plurality of reaction channels, and wherein at least some of the plurality of reaction channels comprise an amount of the hydrophobic material therein.

10. The diagnostic device of illustrative embodiment 9, wherein the substrate comprises a plurality of reaction channels, and wherein the plurality of reaction channels each comprise a dye at an end of the respective channels, wherein the dye is selected to provide a visible or readable indication that a sample introduced to the device has traveled along a length of the reaction channel to the dye.

11. The diagnostic device of illustrative embodiment 10, wherein the dye is reactive with hydrogen peroxide to provide a colorimetric indication.

12. The diagnostic device of illustrative embodiment 9, wherein the plurality of reaction channels are defined by a barrier material and form a predetermined pattern.

13. The diagnostic device of illustrative embodiment 12, wherein the plurality of reaction channels comprise reaction channels having differing concentrations of the hydrophobic material therein.

14. The diagnostic device of 12, wherein the plurality of reaction channels comprise channels having differing lengths.

15. The diagnostic device of any of the preceding illustrative embodiments, wherein the substrate further comprises one or more enzymes disposed thereon.

16. The diagnostic device of illustrative embodiment 14, wherein the target analyte is selected from the group consisting of glucose, lactose, urea, and creatinine, wherein the one or more enzymes comprise one or more enzymes for the breakdown of a member selected from the group consisting of glucose, lactose, urea, and creatinine.

17. The diagnostic device of illustrative embodiment 1, wherein the substrate comprises a plurality of reaction channels, wherein at least some of the plurality of reaction channels comprise an amount of the hydrophobic material and one or more enzymes therein.

18. The diagnostic device of illustrative embodiment 17, wherein the plurality of reaction channels comprise reaction channels having differing concentrations of the one or more enzymes therein.

19. The diagnostic device of illustrative embodiment 1, wherein the hydrophobic material comprises a compound which is converted from the hydrophobic material to the hydrophilic material via reaction with hydrogen peroxide.

20. The diagnostic device of illustrative embodiment 1, wherein the substrate comprises a surface modified with an alkyl ketene dimer as follows:

21. The diagnostic device of illustrative embodiment 1, wherein the hydrophobic material comprises a surface modified with a material which renders the surface hydrophobic.

22. The diagnostic device of illustrative embodiment 1, wherein the hydrophobic material comprises a compound comprising a functional selected from the group consisting of a) Poly(acrylic acid); (b) poly(methacrylic acid); (c) poly(N,N'-diethyl aminoethyl methacrylate); (d) Poly(4-vinylpyridine); (e) Poly(vinyl imidazole); (f) poly[2-(methacryloyloxy)-ethyltrimethylammonium chloride]:

-continued (f)

23. The diagnostic device of illustrative embodiment 1, wherein the hydrophobic material is reactive with a conversion component within or derived from the sample to a degree sufficient to convert the hydrophobic material to a hydrophilic material on the substrate according to acid-catalyzed acetal reaction:

(g)

wherein $R^1$ and $R^2$=a hydrophobic functional group.

24. The diagnostic device of illustrative embodiment 1, wherein the hydrophobic material comprises a compound which is converted from the hydrophobic material to the hydrophilic material via reaction with carbon dioxide.

25. The diagnostic device of illustrative embodiment 1, a compound which is converted from the hydrophobic material to the hydrophilic material via reaction with a thiol.

26. A diagnostic device comprising: a substrate; a plurality of reaction channels defined on the substrate; a hydrophobic material disposed within at least one the reaction channels; and one or more enzymes disposed within at least one of the reaction channels along with the hydrophobic material; wherein the one or more enzymes are selected to provide a conversion component upon contact of the one or more enzymes with a target analyte in a sample introduced to the device; and wherein the hydrophobic material is selected to be converted from the hydrophobic material to a hydrophilic material on the substrate upon contact with the conversion component.

27. The diagnostic device of illustrative embodiment 26, wherein the conversion component is selected from the group consisting of hydrogen peroxide, carbon dioxide, and glutathione.

28. The diagnostic device in any of illustrative embodiments 26-27, wherein the target analyte is selected from the group consisting of glucose, lactose, urea, and creatinine.

29. The diagnostic device of illustrative embodiment 28, wherein the conversion component comprises a member selected from the group consisting of hydrogen peroxide and carbon dioxide.

30. The diagnostic device in any of illustrative embodiments 26-29, wherein the plurality of reaction channels each comprise a dye at an end of the respective channels, wherein the dye is selected to provide a visible or readable indication that a sample introduced to the device has traveled along a length of the reaction channel to the dye.

31. The diagnostic device of illustrative embodiment 26, wherein the one or more enzymes comprise one or more enzymes for the breakdown of a member selected from the group consisting of glucose, lactose, urea, and creatinine.

32. The diagnostic device in any of illustrative embodiments 26-31, wherein the plurality of reaction channels comprise reaction channels having differing concentrations of the one or more enzymes therein.

33. A diagnostic device comprising: a substrate; a plurality of reaction channels defined on the substrate; one or more enzymes disposed within selected ones of the reaction channels; and a dye associated with the reaction channels; wherein the one or more enzymes are selected to provide a conversion component upon contact of the one or more enzymes with a target analyte in a sample introduced to the device; and wherein the conversion component is effective to induce a change in a property of the dye.

34. The device of illustrative embodiment 33, wherein the dye is disposed at an end of the reaction channels.

35. The device of illustrative embodiment 33, wherein the dye is disposed along a longitudinal length of the reaction channels.

36. The device of illustrative embodiment 33, wherein the dye is disposed at intervals along a longitudinal length of the reaction channels.

37. The device in any of illustrative embodiments 33-36, wherein the dye produces a visible or readable change upon reaction with the conversion component.

38. The device in any of illustrative embodiments 33-37, wherein the plurality of reaction channels comprise reaction channels with distinct amounts of the one or more enzymes and same amounts of the dye.

39. The device in any of illustrative embodiments 33-37, wherein the plurality of reaction channels comprise reaction channels with distinct amounts of the dye and same amounts of the reaction channels.

40. The device in any of illustrative embodiments 33-39, wherein the dye reacts with a member selected from the group consisting of hydrogen peroxide, nitric oxide, and a thiol to provide the change in the property.

The invention claimed is:
1. A diagnostic device comprising:
a substrate; and
a hydrophobic material disposed on the substrate;
wherein the hydrophobic material is selected to be converted from the hydrophobic material to a hydrophilic material upon contact with a conversion component within or derived from a sample introduced to the device, wherein the conversion component comprises carbon dioxide; and
wherein the substrate comprises a plurality of reaction channels, and wherein at least some of the plurality of reaction channels comprise an amount of the hydrophobic material therein, and wherein the plurality of reaction channels each comprise a dye at an end of the respective channels, wherein the dye is selected to provide a visible or readable indication that a sample introduced to the device has traveled along a length of the reaction channel to the dye.

2. The diagnostic device of claim 1, wherein the conversion component comprises a target analyte in the sample.

3. The diagnostic device of claim 1, wherein the conversion component comprises a product derived from a reaction with a target analyte in the sample.

4. The diagnostic device of claim 1, wherein the conversion component comprises a component derived indirectly from the target analyte.

5. The diagnostic device of claim 1, wherein the plurality of reaction channels are defined by a barrier material and form a predetermined pattern.

6. The diagnostic device of claim 5, wherein the plurality of reaction channels comprise reaction channels having differing concentrations of the hydrophobic material therein.

7. A diagnostic device comprising:
a substrate; and
a hydrophobic material disposed on the substrate;
wherein the hydrophobic material is selected to be converted from the hydrophobic material to a hydrophilic material upon contact with a conversion component within or derived from a sample introduced to the device, wherein the conversion component comprises a compound having a thiol-terminated group; and
wherein the substrate comprises a plurality of reaction channels, and wherein at least some of the plurality of reaction channels comprise an amount of the hydrophobic material therein, and wherein the plurality of reaction channels each comprise a dye at an end of the respective channels, wherein the dye is selected to provide a visible or readable indication that a sample introduced to the device has traveled along a length of the reaction channel to the dye.

8. The diagnostic device of claim 7, wherein the conversion component comprises a target analyte in the sample.

9. The diagnostic device of claim 7, wherein the conversion component comprises a product derived from a reaction with a target analyte in the sample.

10. The diagnostic device of claim 7, wherein the conversion component comprises a component derived indirectly from the target analyte.

11. The diagnostic device of claim 7, wherein the plurality of reaction channels are defined by a barrier material and form a predetermined pattern.

12. The diagnostic device of claim 11, wherein the plurality of reaction channels comprise reaction channels having differing concentrations of the hydrophobic material therein.

13. A diagnostic device comprising:
a substrate; and
a hydrophobic material disposed on the substrate;
wherein the hydrophobic material is selected to be converted from the hydrophobic material to a hydrophilic material upon contact with a conversion component within or derived from a sample introduced to the device, wherein the conversion component comprises glutathione; and
wherein the substrate comprises a plurality of reaction channels, and wherein at least some of the plurality of reaction channels comprise an amount of the hydrophobic material therein, and wherein the plurality of reaction channels each comprise a dye at an end of the respective channels, wherein the dye is selected to provide a visible or readable indication that a sample introduced to the device has traveled along a length of the reaction channel to the dye.

14. The diagnostic device of claim 13, wherein the conversion component comprises a target analyte in the sample.

15. The diagnostic device of claim 13, wherein the conversion component comprises a product derived from a reaction with a target analyte in the sample.

16. The diagnostic device of claim 13, wherein the conversion component comprises a component derived indirectly from the target analyte.

17. The diagnostic device of claim 13, wherein the plurality of reaction channels are defined by a barrier material and form a predetermined pattern.

18. The diagnostic device of claim 17, wherein the plurality of reaction channels comprise reaction channels having differing concentrations of the hydrophobic material therein.

* * * * *